(12) United States Patent
Freudiger

(10) Patent No.: US 9,149,299 B2
(45) Date of Patent: Oct. 6, 2015

(54) SPINAL IMPLANT SET INCLUDING A QUICK CLOSURE

(75) Inventor: Stefan Freudiger, Bremgarten (CH)

(73) Assignee: SPINESAVE AG (CH)

( * ) Notice: Subject to any disclaimer, the term of this patent is extended or adjusted under 35 U.S.C. 154(b) by 16 days.

(21) Appl. No.: 13/383,615

(22) PCT Filed: Jul. 1, 2010

(86) PCT No.: PCT/CH2010/000169
§ 371 (c)(1),
(2), (4) Date: Jan. 12, 2012

(87) PCT Pub. No.: WO2011/006268
PCT Pub. Date: Jan. 20, 2011

(65) Prior Publication Data
US 2012/0116456 A1    May 10, 2012

(30) Foreign Application Priority Data

Jul. 16, 2009   (CH) ...................................... 1114/09

(51) Int. Cl.
*A61B 17/70* (2006.01)
(52) U.S. Cl.
CPC .................................. *A61B 17/7032* (2013.01)
(58) Field of Classification Search
CPC ............ A61B 17/70; A61B 17/7032–17/7056; A61B 17/8605–17/862; A61B 17/8665
USPC .................. 606/246–278, 300–321
See application file for complete search history.

(56) References Cited

U.S. PATENT DOCUMENTS

| 5,346,493 | A | 9/1994 | Stahurski et al. |
| 6,110,172 | A * | 8/2000 | Jackson ......................... 606/305 |
| 6,139,549 | A * | 10/2000 | Keller ........................... 606/86 A |
| 6,251,112 | B1 * | 6/2001 | Jackson ......................... 606/916 |
| 6,258,090 | B1 | 7/2001 | Jackson |
| 6,302,888 | B1 | 10/2001 | Mellinger |
| 6,652,526 | B1 | 11/2003 | Arafiles |
| 6,786,903 | B2 * | 9/2004 | Lin .................................. 606/23 |
| 6,911,030 | B1 * | 6/2005 | Vanacker et al. ............. 606/270 |
| 7,235,075 | B1 | 6/2007 | Metz-Stavenhagen |
| 7,842,073 | B2 * | 11/2010 | Richelsoph et al. .......... 606/272 |
| 8,236,032 | B2 * | 8/2012 | Ramsay et al. ............... 606/279 |
| 2001/0012937 | A1 * | 8/2001 | Schaffler-Wachter et al. . 606/61 |

(Continued)

FOREIGN PATENT DOCUMENTS

| DE | 4107480 | 9/1992 |
| DE | 9403231 | 6/1994 |

(Continued)

OTHER PUBLICATIONS

International Search Report dated Sep. 10, 2010, issued in corresponding international application No. PCT/CH2010/000169.

(Continued)

*Primary Examiner* — Eduardo C Robert
*Assistant Examiner* — Michelle C Eckman
(74) *Attorney, Agent, or Firm* — Ostrolenk Faber LLP

(57) ABSTRACT

Spinal implant comprising a quick closure (4) for securing a connecting element (2) in a bone screw (1) where the quick closure (4) is rotatively attachable in the clockwise or counterclockwise direction and lockable such as to be able to take up torques applied to the bone screw (1) while preserving the bone anchorage from manipulative stress.

19 Claims, 3 Drawing Sheets

(56) References Cited

U.S. PATENT DOCUMENTS

| | | | |
|---|---|---|---|
| 2002/0120272 A1* | 8/2002 | Yuan et al. | 606/61 |
| 2005/0027292 A1* | 2/2005 | Bernard et al. | 606/61 |
| 2005/0033296 A1* | 2/2005 | Bono et al. | 606/61 |
| 2005/0177154 A1* | 8/2005 | Moumene et al. | 606/61 |
| 2006/0235393 A1* | 10/2006 | Bono et al. | 606/61 |
| 2006/0264933 A1* | 11/2006 | Baker et al. | 606/61 |
| 2008/0058811 A1* | 3/2008 | Alleyne et al. | 606/61 |
| 2009/0048632 A1* | 2/2009 | Firkins et al. | 606/246 |
| 2009/0076550 A1* | 3/2009 | Bernhardt et al. | 606/246 |
| 2009/0082819 A1* | 3/2009 | Blain et al. | 606/308 |
| 2009/0171401 A1* | 7/2009 | Zehnder et al. | 606/301 |
| 2009/0254128 A1* | 10/2009 | Zehnder et al. | 606/302 |
| 2010/0241170 A1* | 9/2010 | Cammisa et al. | 606/264 |
| 2010/0292739 A1* | 11/2010 | Schwab | 606/305 |
| 2011/0160779 A1* | 6/2011 | Schlaepfer et al. | 606/305 |
| 2011/0213419 A1* | 9/2011 | Richelsoph | 606/264 |
| 2012/0215264 A1* | 8/2012 | Lee | 606/305 |
| 2012/0283787 A1* | 11/2012 | Yuan et al. | 606/305 |

FOREIGN PATENT DOCUMENTS

| | | | |
|---|---|---|---|
| EP | 0672388 | 9/1995 | |
| EP | 0836436 | 4/1998 | |
| EP | 1119304 | 8/2001 | |
| EP | 1190678 A2 | 3/2002 | |
| WO | WO 96/39972 | 12/1996 | |
| WO | WO-97/37604 A1 * | 10/1997 | A61B 17/70 |
| WO | WO 00/19923 | 4/2000 | |

OTHER PUBLICATIONS

Notification Concerning Transmittal of International Preliminary Report on Patentability (Chapter I of the Patent Cooperation Treaty) dated Jan. 26, 2012 issued in corresponding International Application No. PCT/CH2010/000169 (6 pages).

* cited by examiner

SPINAL IMPLANT SET INCLUDING A QUICK CLOSURE

CROSS REFERENCE TO RELATED APPLICATIONS

The present application is a 35 U.S.C. §371 National Phase conversion of PCT/CH2010/000169, filed Jul. 1, 2010, which claims benefit of Swiss Application No. 1114/09, filed Jul. 16, 2009, the disclosure of which is incorporated herein by reference. The PCT International Application was published in the English language.

BACKGROUND OF THE INVENTION

The present invention relates to a spinal implant set including a quick closure device according to the preamble of claim 1.

Such closure devices are typically used in the surgical treatment of the spine. As the patients are increasingly aged, they have more often porotic bones, thereby limiting the anchoring ability of screws. It is therefore particularly important that connecting elements can be fastened in screw heads with minimum stress, ideally in such a manner that the screw anchorage in the bone remains unaffected.

Various quick closures are known in the art, all of which suffer from one or several drawbacks, however, as shown below.

For their comparative assessment, quick closures of the prior art are classified as follows: Internally or externally slidingly attachable quick closures, internally or externally rotatively attachable quick closures, as well as internal and external bayonet-like quick closures. Also, a vertically snapping quick closure is referenced in the prior art.

Among the internally slidingly attachable quick closures, the following ones are e.g. known in the art: EP0672388 (Metz-Stavenhagen et al., 1995), slidingly insertable with an end stop in the insertion direction; U.S. Pat. No. 6,110,172 (Jackson, 1998), insertable from two directions with an end stop in both directions after raising the cap; U.S. Pat. No. 6,302,888 (Mellinger, 1999), insertable without end stops. EP0836436 (Wisnewski et al., 1995), not only slidingly but pivotably insertable without end stops.

Among the externally slidingly attachable quick closures, the following ones are e.g. known in the art: DE4107480 (Ulrich et al., 1991) and U.S. Pat. No. 6,139,549 (Keller, 1997), insertable at the bottom of the screw head near the bone thread without stops and with high space requirement.

Among the internally rotatively attachable quick closures, the following ones are e.g. known in the art: EP1119304 (Yuan, 1998), rotatively insertable in one direction with an end stop; U.S. Pat. No. 6,258,090 (Jackson, 2000), rotatively insertable in one direction without an end stop; U.S. Pat. No. 6,652,526 (Arafiles, 2001), rotatively insertable in two directions without an end stop; U.S. Pat. No. 6,786,903 (Lin, 2002), rotatively insertable in two directions with a positioning aid on the rod.

Among the externally rotatively attachable quick closures, the following ones are e.g. known in the art: U.S. Pat. No. 5,346,493 (Stahurski et al., 1993), rotatively insertable in both directions without an end stop; U.S. Pat. No. 6,251,112 (Jackson, 2000), rotatively insertable in one direction without an end stop; EP1190678 (Bono et al., 2001), rotatively insertable in one direction with an end stop.

Among the internal and external bayonet-like quick closures, the following ones are e.g. known in the art: DE9403231 (Aesculap, 1994), insertable at the bottom of the screw head from one side, with an end stop; U.S. Pat. No. 7,235,075 (Metz-Stavenhagen, 2003), insertable at the top of the screw head from one side, with an end stop.

A snapping quick closure is proposed by US 2005/0027292 (Bernard et al., 2005).

In this respect, a main disadvantage of slidingly insertable quick closures is that relatively high moments have to be applied to the typically long instruments used in spinal surgery by the surgeon with the risk of creating uncontrolled situations at the location of the screw. For rotatively insertable quick closures, the required torque along the instrument always remains the same. A rotational insertability from two sides is therefore important as due to the increasingly frequent application of dynamic stabilizing systems, plastic rods are being used more and more frequently. They are, however, larger than metal rods for reasons of stability and therefore require more space.

In situations of limited space at the pedicle entrance, a quick closure that is rotatively insertable from only one side may lead to collisions with transverse processes or facet joints, which is less probable in the case of a rotational insertability from two sides. With quick closures without end stops, screws cannot be tightened without being retained by an additional instrument for which the access to the screw is difficult. Consequently, an end stop in the tightening direction preserves the bone bed while fastening the clamping screw whereas an end stop against the tightening direction preserves the bone bed while releasing the clamping screw. An end stop in both directions optimally preserves the bone bed in both directions.

A major disadvantage of a metallic snapping mechanism are the required macroscopic elastic deformation achievable only through limited local strength and the rather complicated instruments required to unlock a snapped-in junction while demanding important removal forces with the risk of overloading the elastic elements. Also the tightening screw of Bernard et al. does not have a matching seat in the screw head and consequently cannot transfer the rod's load directly into the screw head, but must rather transfer them through the threads of the closure.

Also as a result of the increasing dimensions of plastic rods for dynamic stabilizing systems, the space left between the screw head and the pedicle entrance is mostly insufficient for a quick closure coupling. In such cases, only systems are applicable where the quick closure is arranged at the top of the screw head.

SUMMARY OF THE INVENTION

Thus, an object of the present invention is to design a spinal implant set including a quick closure for fastening a connecting element in a bone screw in such a manner that it is easier to assemble and better protects the bone bed of the bone screw from manipulative stress.

Such an implant set is suggested according to claim 1. The further claims define preferred embodiments thereof.

Accordingly, the quick closure is attachable in two directions (clockwise and counterclockwise direction) and subsequently lockable so as to be able to take up torques acting upon the screw in both directions.

Preferably, the invention proposes the quick closure defined in claim 1, which is rotatively attachable over protrusions on the screw head from the left or from the right. Furthermore, the rotative attachment of the quick closure in the screw head may be assisted by centering properties of the preassembled clamping element.

In a preferred use, the quick closure is retracted manually or by means of a clamping screw so that hooks of the quick closure engage in protrusions of the screw head and a filler of the quick closure in a recess of the protrusion of the screw head and lock therewith. In this manner, torques transmitted from the clamping element to the bone screw can be taken up by the quick closure without applying additional stresses to the bone bed of the bone screw. Furthermore, due to its guidance in the screw head, the clamping element is able to directly transmit longitudinal forces from the connecting element to the bone screw.

BRIEF DESCRIPTION OF THE DRAWINGS

The present invention is explained in more detail hereinafter by means of a preferred exemplary embodiment with reference to the appended drawings which merely illustrate the exemplary embodiment.

The drawings schematically show:

FIG. 1 3D-view of an implant set assembly.

DESCRIPTION OF PREFERRED EMBODIMENTS

Figure 1:
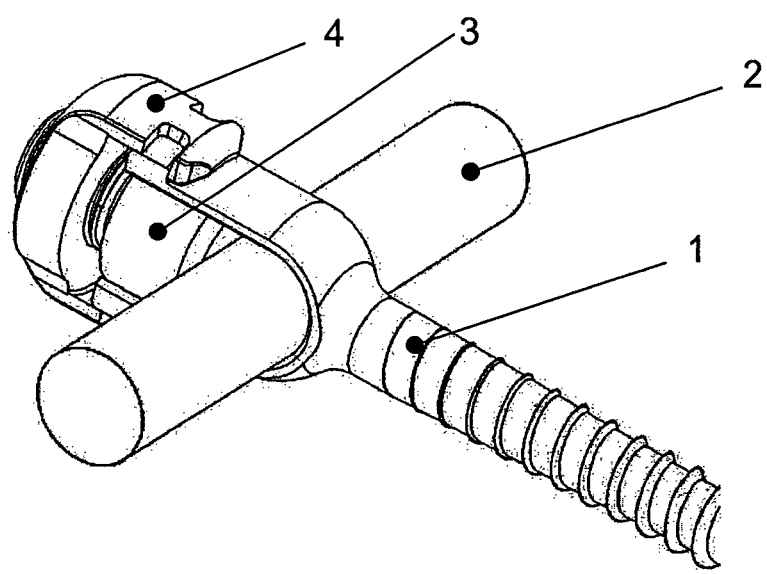

FIG. 1 illustrates the bone screw 1, the connecting element 2, the clamping element 3, and the quick closure 4 in the assembled state.

Figure 2A:
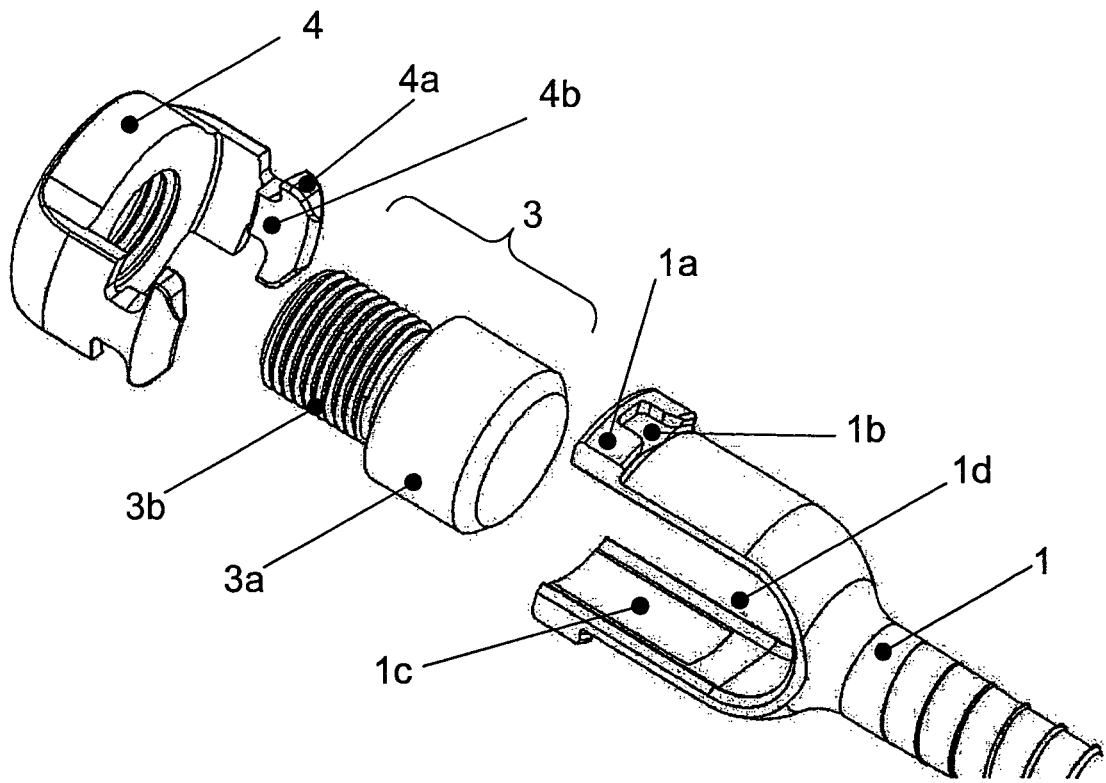
FIG. 2a an exploded view of the bone screw, the quick closure, and the clamping element.

FIG. 2a illustrates the bone screw 1 with the screw head protrusions 1a, the recess 1b between the protrusions 1a, and the clamping element guide 1c on one half of the bone screw head, as well as the seat 1d of a connecting element; the clamping element 3 with its surface 3a that fits the clamping element guide 1c and its threaded portion 3b; the quick closure 4 with its hooks 4a that fit the screw head protrusions 1a and its filler 4b that fits the recess 1b.

Figure 2B:
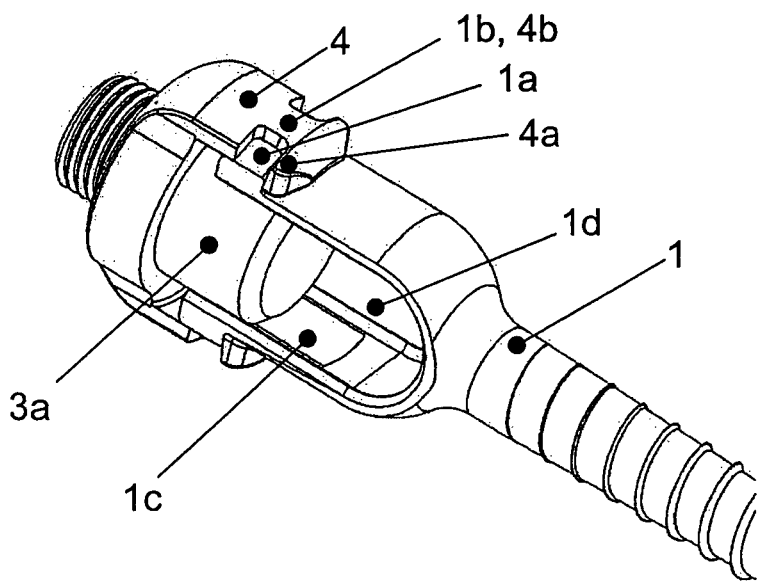
FIG. 2b an assembly drawing of the bone screw, the quick closure, and the clamping element.

FIG. 2b illustrates the bone screw 1 with the hooks 4a abutting the screw head protrusions 1a from below 1a, the filler 4b of the quick closure 4 inserted in the recess 1b, and the clamping element surface 3a of the clamping element 3 inserted in the clamping element guide 1c.

Figure 3A:
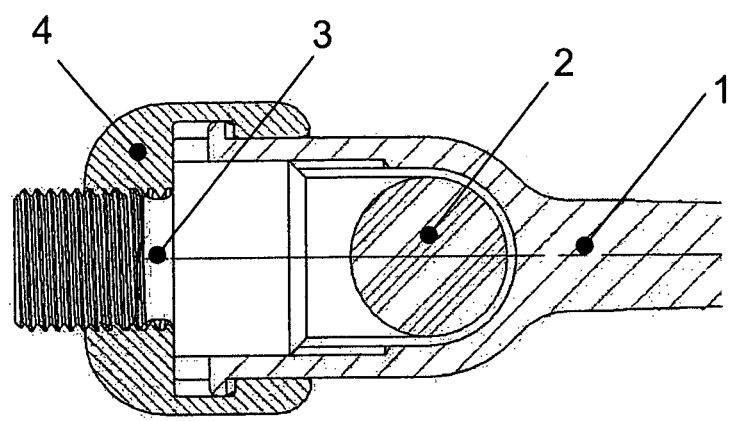
FIG. 3a a sectional view of the locked and non-clamped quick closure.

FIG. 3a illustrates a longitudinal section of the bone screw 1 with the connecting element 2, the clamping element 3, and the cross-section of the quick closure 4 in the locked but non-clamped state.

Figure 3B:
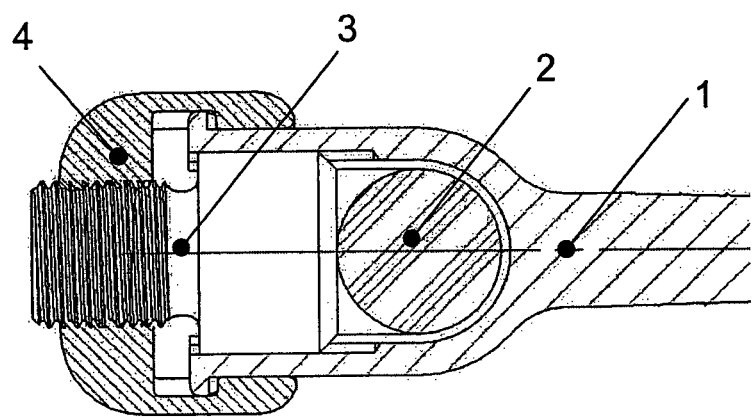
FIG. 3b a sectional view of the locked and clamped quick closure.

FIG. 3b illustrates the longitudinal section of the bone screw 1, of the connecting element 2, the clamping element 3, and the cross-section of the quick closure 4 in the locked and clamped state.

This assembly provides a quick and secure attachment of a connecting element 2 in a pedicle screw 1.

Notably, the clamping element guides is cover a sufficient wrap angle that the clamping element 3 is safely held even in the longitudinal direction of the connecting element 2.

For use of the closure, the connecting element 2 is placed in the head 1a of the bone screw 1. The quick closure 4 with the clamping element 3 in a retracted position is set on the screw head in sliding the connecting element down the clamping element guides 1c. Quick closure 4 is set on the head in a position that the locking extensions bearing the hooks 4a and the filler 4b pass between the screw head protrusions 1a or stops arrangements. The quick closure 4 is turned so that the fillers 4b slide into recesses 1b when the quick closure 4 is retracted. This backward movement is limited by the hooks 4a hitting the protrusions 1a. Then, the clamping element 3 is screwed down using a tool attached to the accessible end of the threaded portion 3b. Once it hits the connecting element 2 (cf. FIG. 3b), it will exert a force on the connecting element 2 as well as on the quick closure 4 keeping both in their locked position. The quick closure 4 is now locked by positive interlockings: In axial direction, the hooks 4a engage with the screw head protrusions 1a, and a rotation in both directions is inhibited by the filler 4b resting in the recess 1b between the head protrusions 1a providing stop faces on both sides of the filler 4b.

Based on the aforegoing description the one skilled in the art is able to derive modifications without leaving the scope of protection which is defined by the claims.

What is claimed is:

1. A spinal implant set comprising:
a connecting element;
at least one bone screw, the bone screw having a longitudinal extent in an axial direction and comprising a head with a seat for the connecting element;
a quick closure element comprising a locking arrangement forming a T shape comprising at least a hook portion and a filler portion including a first side and a second side;
a clamping element,
wherein the head of the bone screw comprises a curvilinear outward lateral face and a stop arrangement comprising at least one axial stop face, a first twist stop face comprising a first side of an outward lateral surface of the stop arrangement, and a second twist stop face comprising a second side of the outward lateral surface of the stop arrangement, the second side of the outward lateral surface facing the first side of the outward lateral surface, the first and second sides each extending substantially parallel to the axial direction;
the clamping element is positioned and configured to be inserted in the head of the bone screw and includes an adjustable connection with the quick closure element; and
the hook portion comprising a curvilinear inner surface configured to face the curvilinear outward lateral face, so as to enable twisting of the hook portion on the head of the bone screw,
wherein after the twisting, the hook portion is retractable axially to a locked position in which the hook portion engages axially with the axial stop face and the filler portion engages circumferentially and in a bidirectional manner, both clockwise and counterclockwise, with the two twist stop faces, such that the first side of the filler portion faces the first twist stop face, and the second side of the filler portion faces the second twist stop face, the quick closure element in the locked position being attached to the bone screw; and
the clamping element is configured to be adjusted to create an axial force between the head of the screw and the quick closure element after the connecting element is placed in the head of the screw, and thus the quick closure element is locked against axial removal from and clockwise and counterclockwise rotation with respect to the bone screw.

2. The spinal implant set according to claim 1, wherein the axial stop face and the twist stop faces comprise at least two protrusions producing a circumferential recess in between, the at least two protrusions being positioned and configured such that respective faces of the protrusions delimiting the recess comprise the twist stop faces.

3. The spinal implant set according to claim 2, wherein a width of the circumferential recess matches the filler portion, and the circumferential recess is positioned and configured to lock the quick closure element against rotation in a substantially play-free manner.

4. The spinal implant according to claim 1, wherein the quick closure element comprises:
at least two hook portions, the hook portions being circumferentially displaced; and
the filler portion being arranged about circumferentially centered between the hook portions.

5. The spinal implant set according to claim 4, wherein the at least two hook portions and the filler portion are positioned in an axial configuration such that the at least two hook portions and the filler portion form a T-shape.

6. The spinal implant set according to claim 1, wherein the hook portion and the filler portion protrude on at least one extension of the quick closure element, the at least one extension being shaped to extend over an outward surface of the head of the bone screw.

7. The spinal implant set according to claim 1, wherein the head of the bone screw comprises a second stop arrangement comprising:
at least one axial stop face; and
at least two twist stop faces on the outward lateral surface, the second stop arrangement positioned on an opposite side of the head; and
the quick closure element comprises a second closure locking including a hook portion and a filler portion.

8. The spinal implant set according to claim 1, wherein the adjustable connection comprises a threaded portion of the clamping element and a corresponding threaded hole in the quick closure element.

9. The spinal implant set according to claim 1, wherein the head of the bone screw comprises:
an axial slide guide for the clamping element, the axial slide guide positioned and configured to inhibit a radial movement of the clamping element.

10. The spinal implant set according to claim 9, wherein the axial slide guide comprises at least two axially extending wall portions of the screw head with an inner surface corresponding to a cross-section of the clamping element and covering each an effective angle.

11. The spinal implant set according to claim 10, wherein the at least two axially extending wall portions are shaped as partial cylinder walls enabling rotation of the clamping element.

12. The spinal implant set according to claim 9, wherein the clamping element centers the quick closure by guidance in the head of the bone screw in the longitudinal axis of the screw.

13. The spinal implant set according to claim 9, wherein the clamping transmits forces along the longitudinal axis of the connecting element from the connecting element to the bone screw by guidance in the head of the bone screw in the longitudinal axis of the bone screw.

14. The spinal implant set according to claim 1, wherein the connecting element is a rod.

15. The spinal implant set according to claim 14, wherein the rod is round.

16. The spinal implant set according to claim 1, wherein the connecting element is made of metal.

17. The spinal implant set according to claim 1, wherein the clamping element comprises a cylindrical stem and of a threaded portion.

18. The spinal implant set according to claim 1, wherein the quick closure engages the end of the head of the bone screw opposite the thread of the bone screw.

19. The spinal implant set according to claim 1, wherein the connecting element is made of a plastic material.

\* \* \* \* \*